(12) United States Patent
Makino et al.

(10) Patent No.: US 6,506,567 B2
(45) Date of Patent: Jan. 14, 2003

(54) WATER-SOLUBLE FLOURESCENT INTERCALATOR COMPOUND

(75) Inventors: Yoshihiko Makino, Saitama (JP); Masashi Ogawa, Tokyo (JP); Makoto Takagi, Fukuoka (JP); Shigeori Takenaka, Fukuoka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/774,895

(22) Filed: Jan. 31, 2001

(65) Prior Publication Data

US 2001/0014452 A1 Aug. 16, 2001

(30) Foreign Application Priority Data

Jan. 31, 2000 (JP) .................................... 2000-022181

(51) Int. Cl.[7] ................................................. C12Q 1/68
(52) U.S. Cl. ................................. 435/6; 436/94; 540/1
(58) Field of Search ........................... 435/6; 436/94; 540/1

(56) References Cited

U.S. PATENT DOCUMENTS

| | | | | |
|---|---|---|---|---|
| 5,593,829 A | * | 1/1997 | McCabe | 435/6 |
| 5,698,408 A | * | 12/1997 | Rokos | 435/7.9 |
| 5,731,148 A | * | 3/1998 | Becker et al. | 435/6 |
| 6,261,780 B1 | * | 7/2001 | Ogawa et al. | 435/6 |
| 6,294,670 B1 | * | 9/2001 | Takenaka | 544/225 |

* cited by examiner

*Primary Examiner*—Kenneth R. Horlick
(74) *Attorney, Agent, or Firm*—Reed Smith LLP

(57) ABSTRACT

A water-soluble fluorescent intercalator compound having the formula:

$$F-La-X$$

Figure 1:
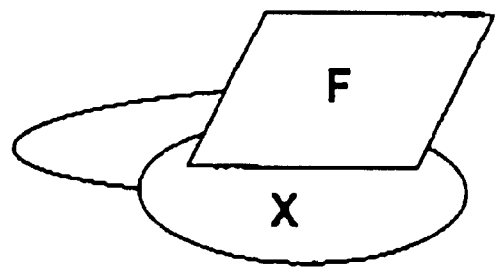

F is a fluorescent moiety, X is a divalent cyclic group, and La is a linking group, and at least one of X and La has a site imparting water solubility to the compound or a site that is convertible into a site imparting water solubility to the compound is favorably employable as a fluorescent intercalator in a method for fluorometrically detecting complementary DNA fragments.

22 Claims, 1 Drawing Sheet

(b)　　　　　　　　　　(c)

(a)

(b)  (c)

WATER-SOLUBLE FLOURESCENT INTERCALATOR COMPOUND

This application claims Paris Convention priority of Japanese Patent Application No. 2000-022181 filed Jan. 31, 2000, the complete disclosure of which is hereby incorporated by reference.

FIELD OF THE INVENTION

The present invention relates to a fluorescent intercalator compound which is favorably employable in a procedure of analyzing oligonucleotides or polynucleotides such as DNA fragments by fluorometry.

BACKGROUND OF THE INVENTION

In the gene analysis in the fields of biochemistry and clinical test, the detection of a DNA or its fragment having a specific base sequence is performed by way of a hybridization method, particularly Southern hybridization method (Southern blotting method). Southern hybridization is performed using a radioisotope (RI) label. The conventional analytical methods using radioisotope label such as Southern hybridization method appear to be disadvantageous in that they need troublesome radioisotopes.

Recently, the hybridization is generally performed using a DNA chip in which a group of probe molecules of nucleotide derivatives or their analogues (such as PNA) are fixed on a substrate.

A Southern hybridization method using a fluorescent label in place of a radioisotope label is also known. This method appears to be superior to the method using RI in safety and rapidness in obtaining analytical results. Therefore, DNA chips comprising a substrate such as a slide glass or a silicone plate and a great number of oligonucleotide or polynucleotide molecules (i.e., probe molecules) fixed onto the substrate are now commercially available for the use in the fluorescence detection systems.

In the well known fluorescence detection system, a fluorescent label is attached to a target DNA fragment (i.e., DNA fragment to be analyzed in its base sequence). Thus labeled target DNA fragment is brought into contact with probe molecule of a DNA chip. If the target DNA fragment is complementary to the probe molecule, the target DNA fragment is combined with the probe molecule and hence fixed to the DNA chip. The DNA chip to which the target DNA fragment having fluorescent label is fixed is detected by fluorometry. This means that the question on whether or not the target DNA fragment is complementary to the probe molecule of the DNA chip is answered.

Recently, a new fluorescence detection system in which a fluorescent intercalator is utilized is developed. The new system is performed by the process including the following steps:
  bringing a group of probe molecules fixed on a substrate into contact with oligonucleotide samples or polynucleotide samples in an aqueous medium in the presence of a fluorescent intercalator so as to form by hybridization a complex of the group of probe molecules and the oligonucleotide samples or polynucleotide samples on the substrate in which the fluorescent intercalator compound is intercalated; and
  detecting a fluorescence emitted from the fluorescent intercalator compound intercalated into the hybridized complex on the substrate.

Bull. Chem. Soc. Jpn., 72, 327–337 (1999) indicates a compound having two fluorescent acridine dye such as N,N-bis{3-[4-(3-(6-chloro-9-imino-2-methoxyacridinyl)-propyl)-1,4-diazacyclohexyl]propyl}naphthalenediimide which is represented by the below-illustrated formula is employable as the fluorescent intercalator.

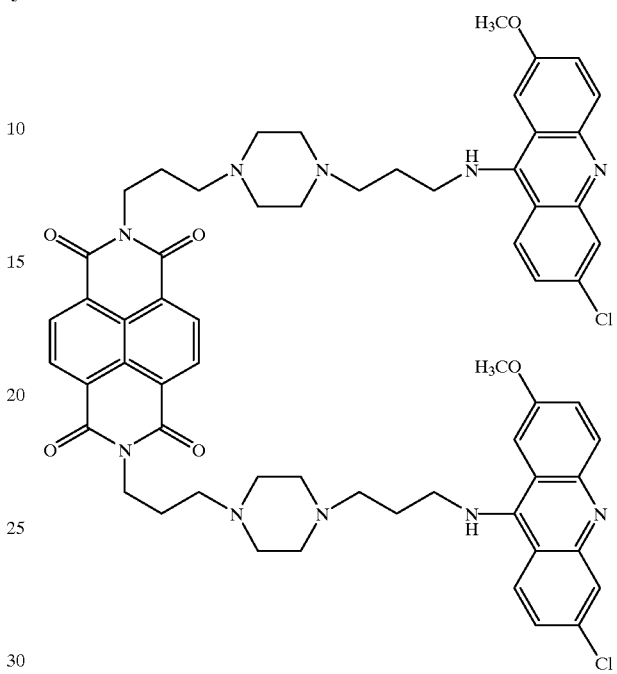

According to the study of the present inventors, it has been confirmed that when a fluorescent intercalator is brought in contact with a hybrid structure in an aqueous medium, a portion of the intercalator is intercalated into the hybrid structure and other portion remains in the aqueous medium without being intercalated into the hybrid structure In other words, equilibrium is present when an intercalator is kept in contact with a hybrid structure in an aqueous medium.

Accordingly, not only the fluorescent intercalator intercalated into the hybrid structure but also the fluorescent intercalator remaining in the aqueous medium emit fluorescence, and hence it is not easy to fluorometrically differentiate fluorescence emitted by the intercalator intercalated into the hybrid structure from fluorescence emitted by the intercalator dissolved in the aqueous medium. Therefore, in the presence of the aqueous medium containing the fluorescent intercalator, the hybridization is not clearly detected. In other words, S/N (signal/noise) ratio is not satisfactory high, so long as the above-mentioned fluorescent intercalator compound is employed.

Accordingly, it is an object of the present invention to provide a new fluorescent intercalator compound which is favorably employable in processes for fluorometrically detecting oligonucleotide samples or polynucleotide samples complementary to a group of probe molecules of nucleotide derivatives or their analogues fixed onto a substrate.

SUMMARY OF THE INVENTION

The present invention resides in a water-soluble fluorescent intercalator compound having the formula (I):

$$F\text{—}La\text{—}X \tag{I}$$

in which F is a fluorescent moiety, X is a cyclic group, and La is a linking group, in which at least one of X and La has a site imparting water solubility to the compound or a site that is convertible into a site imparting water solubility to the compound.

In the formula (I), X preferably has a substituent group represented by the formula of —Lb—Z, in which Z is a non-fluorescent moiety and Lb is a linking group.

The present invention further resides in a process for fluorometrically detecting oligonucleotide samples or polynucleotide samples complementary to a group of probe molecules of nucleotide derivatives or their analogues fixed onto a substrate, which comprises the steps of:

bringing the group of probe molecules into contact with oligonucleotide samples or polynucleotide samples in an aqueous medium in the presence of a fluorescent intercalator compound of the formula (I) so as to form by hybridization a complex of the group of probe molecules and the oligonucleotide samples or polynucleotide samples on the substrate in which the fluorescent intercalator compound is intercalated; and detecting a fluorescence emitted from the fluorescent intercalator compound intercalated into the hybridized complex on the substrate.

Furthermore, the invention resides in a process for fluorometrically detecting oligonucleotide samples or polynucleotide samples complementary to a group of probe molecules of nucleotide derivatives or their analogues fixed onto a substrate, which comprises the steps of:

bringing the group of probe molecules into contact with oligonucleotide samples or polynucleotide samples in an aqueous medium so as to form by hybridization a complex of the group of probe molecules and the oligonucleotide samples or polynucleotide samples on the substrate;

bringing a fluorescent intercalator compound of the formula (I) into contact with the hybridized complex on the substrate, whereby the fluorescent intercalator compound is intercalated into the hybridized complex; and detecting a fluorescence emitted from the fluorescent intercalator compound intercalated into the hybridized complex on the substrate.

BRIEF EXPLANATIIN OF DRAWINGS

FIG. 1 schematically illustrates an assumed condition of the fluorescent intercalator in an aqueous medium.

Figure 2:
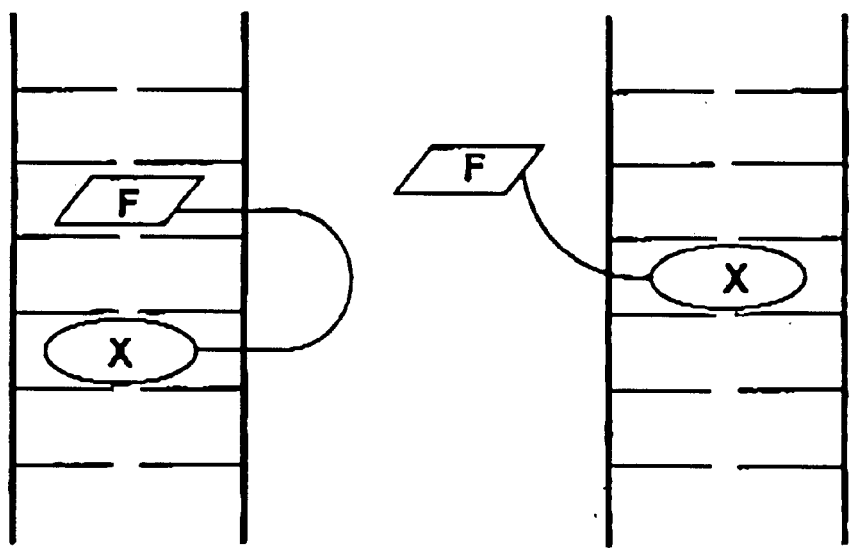

FIG. 2 schematically illustrates assumed conditions of the fluorescent intercalator in a hybrid complex.

DETAILED DESCRIPTION OF THE INVENTION

In the formula (I), F is a fluorescent moiety (i.e., fluorescence-emitting moiety). The fluorescent moiety generally emits a fluorescence in the wavelength region of 400 to 700 nm, preferably 400 to 550 nm.

A preferred example of the fluorescent moiety is a moiety having an acridine group, an indocyanine group, or an azaindoleninecyanine group. Also preferred is a groove binder group which has a quaternary cation in its molecular structure. The groove binder shows strong interaction with the anion of phosphate ester moiety of DNA fragment attached to a probe molecule of a DNA chip.

Representative examples of indocyanine groups (II), or azaindoleninecyanine groups (III), acridine groups (IV), and groove binder group (V) are illustrated below (A is oxygen atom or sulfur atom):

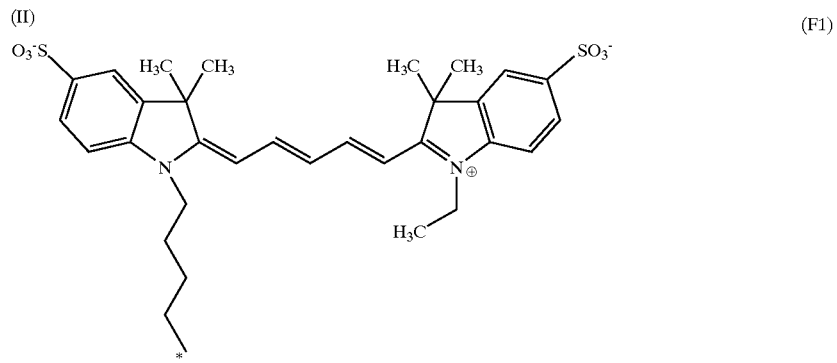

(II) (F1)

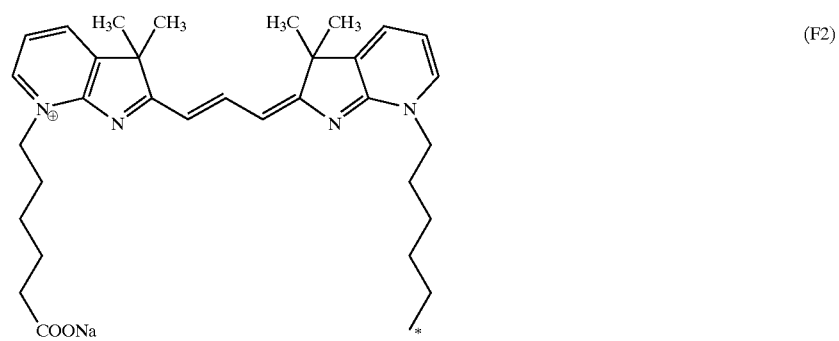

(F2)

(III)
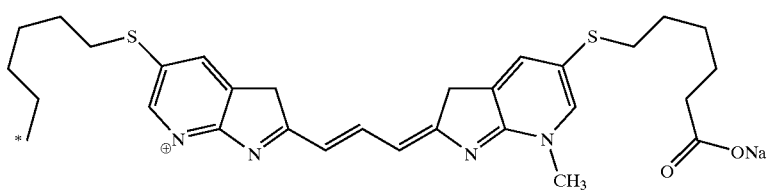
(III)
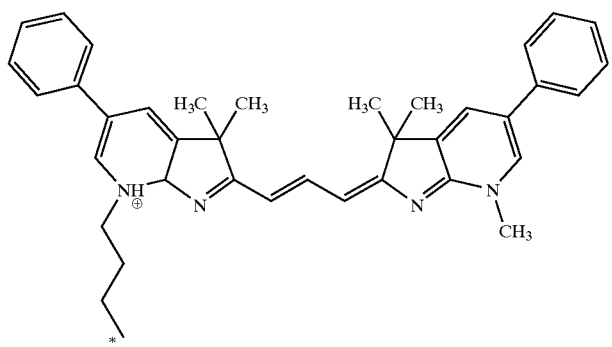
(IV)
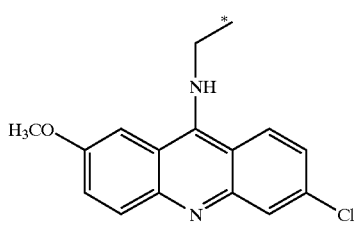
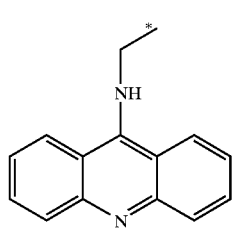
(V)
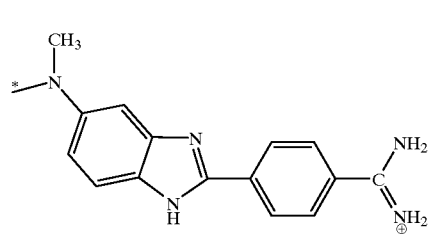
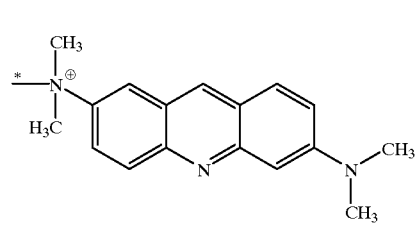

(V)

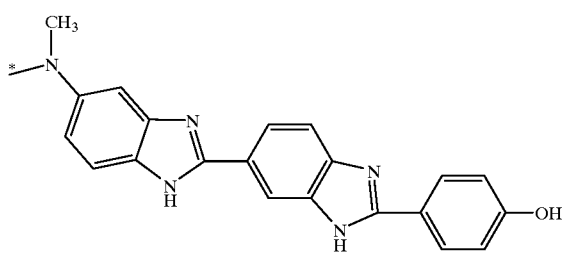

(F9)

(V)

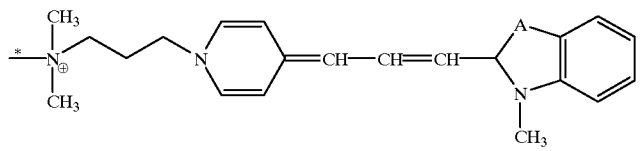

(F10)

(V)

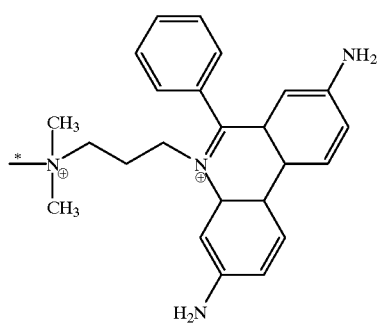

(F11)

In the formula (I), X represents a cyclic group which may have one or more substituents. The cyclic group preferably is a plane cyclic group.

Examples of the cyclic groups include aromatic group having condensed aromatic rings such as a naphthalene diimide group having a bonding site at its nitrogen atom, an anthracene group having a bonding site at 1-, 2-, 5-, or 6-position (preferably 2- or 6-position), an anthraquinone group having a bonding site in the same manner as in the anthracene group, a fluorene group having a bonding site at 2- or 6-position, a biphenylene group having a bonding site at 2- or 6-position, a phenantholene group having a bonding site at 2 or 7-position, and a pyrene group having a bonding site at 2- or 7-position. Preferred is a naphthalene diimide group, an anthraquinone group, or an anthracene group.

The substituent can be a halogen atom (e.g., F, Cl, or Br), or an alkyl group having 1 to 6 carbon atoms such as methyl, ethyl, or n-propyl.

Representative examples of X are illustrated below, in which the asterisk means a possible bonding site:

(X1)

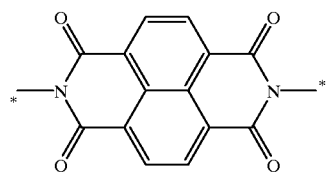

-continued (X2)

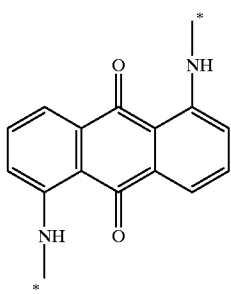

(X3)

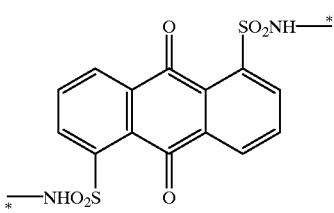

In the formula (I), it is preferred that La, i.e., linking group, has no aromatic group, and preferably contains one or more of an imino group, a 1,4-piperazinyl group, —O—, —S—, —CONH—, and —SO$_2$—.

La preferably contains a hydrocarbyl group (which may have one or more substituents) such as an alkylene group having 1 to 6 carbon atoms or an alkenylene group having 2 to 6 carbon atoms Examples of the substituents for La include hydroxyl, halogen, carboxyl, amino, cyano, nitro, $formyl_1$, formylamino, alkyl having 1 to 6 carbon atoms, alkylamino having 1 to 6 carbon atoms, halogenated alkyl having 1 to 6 carbon atoms, cycloalkylamono having 5 to 7 carbon atoms, dialkylamino having 2 to 12 carbon atoms, aryl having 6 to 12 carbon atoms, aralkyl having 7 to 18 carbon atoms which contains alkyl of 1–6 carbon atoms, aralkylamino having 7 to 18 carbon atoms which contains alkyl of 1–6 carbon atoms, alkanoyl having 2 to 7 carbon atoms, alkanoylamino having 2 to 7 carbon atoms, N-alkanoyl-N-alkylamino having 3 to 10 carbon atoms, aminocarbonyl, alkoxycarbonyl having 2 to 7 carbon atoms, heterocyclic ring having 2 to 10 carbon atoms which has 1 to 4 hetero atoms such as S, N, or O, and aryl having 6 to 12 carbon atoms in its ring structure which may have 1 to 5 substituents such as alkyl of 1–6 carbon atoms, alkoxy of 1–6 carbon atoms, or halogen. The number of the substituents preferably is in the range of 1 to 12, more preferably 1 to 3, when the main chain is an alkylene group having 1 to 6 carbon atoms. The number of the substituents preferably is in the range of 1 to 10, preferably 1 to 3, when the main chain is an alkenylene group having 2 to 6 carbon atoms.

La may contain one or more groups such as an amino bonding, an ester bonding, an ether bonding, a thioether bonding, a diimide bonding, a thiodiimide bonding, a thioamide bonding, an imino bonding, a carbonyl bonding, a thiocarbonyl bonding, or 1,4-piperazinyl bonding, any bonding possibly having one or more substituents.

The main chain of La (which means a chain along the shortest connection route from F to X) preferably contains 2 to 50 atoms, more preferably 5 to 30.

La preferably contains a site imparting water solubility to the compound or a site that is convertible into a site imparting water solubility to the compound. The site that is convertible into a site imparting water solubility to the compound means such site that it can be converted into a site imparting water solubility to the compound, for instance, by contact with an aqueous acidic solution such as an aqueous sulfuric acid. For instance, an imino group having a methyl substituent can be converted into a site having a sulfate group by contact with sulfuric acid. Thus formed site having a sulfate group imparts to the compound a necessary water solubility. The site can have an electric charge.

The water solubility can be introduced by producing the intercalator compound in the form of a water soluble salt, such as hydrochloride, sulfate, carbonate, phosphate, hydrobromide, hydroiodide, acetate, oxalate, malonate, succinate, maleate, fumarate, lactate, malate, citrate, tartrate, methanesulfonate, sodium salt, potassium salt, calcium salt, magnesium salt, pyridinium salt, ammonium Salt, triethylamine salt, or ethanol amine salt.

The water solubility is required for the compound in the case that the compound functions in an aqueous medium as the intercalator.

In the formula (I), X can have a substituent group represented by —Lb—Z in which Z is a non-fluorescent moiety, preferably a non-fluorescent, non-aromatic moiety, which can contain oxygen, nitrogen and/or sulfur. More preferably, Z is a non-fluorescent moiety, preferably a non-fluorescent, non-aromatic moiety, which can contain an amino group, a carboxyl group, a sulfonic acid group, a sulfinic acid group, a sulfenic acid group, a hydrazino group, a carbamoyl group, a hydroxyl group, an imino group, and/or a mercapto group.

Lb is essentially the same as or similar to La of the formula (I). The resulting main chain of La—X—Lb preferably contains 10 to 100 atoms, which are counted along the shortest connection route from F to Z.

The fluorescent intercalator compound of the invention can be prepared in a manner similar to that described in Japanese Patent Provisional Publication 9-288080.

It is assumed that the fluorescent intercalator compound of the formula (1) is generally present in an aqueous medium in the form illustrated in FIG. 1(a). The intercalator compound in the form of FIG. 1(a), specifically, the fluorescent moiety P, emits a relatively weak fluorescence by the presence of a disturbing plane group of X. The fluorescent moiety F and the plane group X probably form in conjunction with each other a stack structure illustrated in FIG. 1(a).

When the intercalator compound of the formula (I) is brought into contact with a hybrid structure (i.e., hybridized complex), it is intercalated in the form of FIG. 2(b) or FIG. 2(c). In each form, the fluorescent inter- calator, specifically, the fluorescent moiety F, emits a strong fluorescence because no disturbing moiety such as X is not stacked on the fluorescent moiety F.

In the detection of DNA fragments, a DNA chip having a substrate and a group of probe molecules fixed to the substrate is employed.

The probe molecule which is a single stranded DNA fragment can be obtained from DNA or its fragment which is obtained by extraction from a living body, cleavage by restriction enzyme, separation by electrophoresis, and denaturation by heat-treatment or alkaline-treatment. The single stranded oligonucleotide can be chemically synthesized. In any case, it is preferred that the single stranded probe oligonucleotide such as DNA fragment for the probe molecules is previously analyzed for base sequencing according to the known methods.

The probe molecule is then fixed onto an substrate such as glass, plastic plate, a coated glass, etc.

The hybridization is carried out in the presence of the fluorescent intercalator of the invention, which is preferably used in a concentration of several nM to several mM. The intercalator can accelerate the hybridization between the probe oligonucleotide and a sample DNA fragment and per se inserts into the complex structure of the hybridized DNA so that the hybridized DNA is stabilized.

The fixation of the DNA tragment sample to the probe molecule of the substrate can be detected by fluorometry.

The intercalator of the invention can be also favorably employable for detecting DNA fragment samples which are partly complementary to the probe molecules Such fragment samples are generally referred to as "mis-match fragment". The detection of the mis-match fragment can be performed by comparing the fluorescence strength in the detection of the possibly mis-matched DNA fragment with the fluorescence strength obtained in the detection of a fully complementary DNA fragment (i.e., full-match fragment).

The present invention is further described by the following examples.

[Preparation of fluorescent intercalator—N-{3-[4-(3-(6-chloro-9-imino-2-methoxyacridinyl)propyl)-1,4-diazacyclohexyl]propyl}-N'-{3-[4-(3-aminopropyl)-1,4-diazacyclohexyl]propyl}naphthalenediimide]

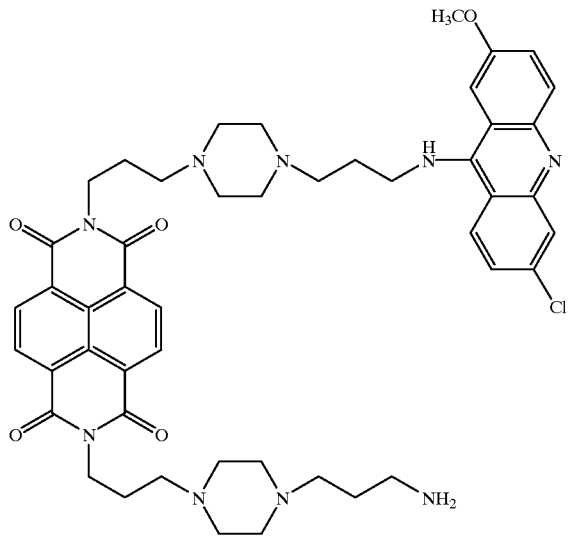

In a 200 mL-volume egg-plant type flask equipped with a reflux condenser were placed naphthalene-1,4,5,8- tetracarboxylic acid dihydrate (1 g, 3.7 mmol.) and N,N'- bis(3-aminoprcpyl)piperazine (20 mL, 9.2 mmol.). Into the flask was further placed tetrahydrofuran (15 mL), and the compounds were dissolved in tetrahydrofuran. The resulting solution was refluxed for 8 hours, and then cooled to room temperature. The reaction mixture was poured into one liter of ether, and the resulting precipitate was collected by filtration using a glass filter (G4). The collected precipitate was dissolved in a mixture of chloroform and methanol to remove attached N,N'- bis(3-aminopropyl)piperazine. The solution was then poured into ether. The resulting crystalline precipitate was collected by filtration and dried under reduced pressure.

The dry crystalline precipitate (0.52 g, 0.8 mol.) and 6,9-dichloro-2-methoxyacridine (0.53 g, 1.9 mmol.) were placed in a 200 mL-volume egg-plant type flask. Into the flask was further placed phenol (15 mL), and the compounds were dissolved in phenol. The resulting solution was heated at a temperature of 100 to 130° C. for 8 hours, and cooled to room temperature. To the reaction mixture was added aqueous 1 M sodium hydroxide solution (50 mL), and the resulting mixture was subjected to extraction using chloroform. The chloroform portion was dried over anhydrous sodium sulfate, and then the solvent was removed by placing the dry chloroform portion under reduced pressure. The residue was dissolved in a minimum amount of chloroform, and the chloroform solution was placed in ether (1 liter). The resulting crystalline precipitate was collected by filtration using a glass filter and the collected precipitate was dried under reduced pressure. The dry precipitate was purified by chromatography to give the desired product, yield: 37%.

EXAMPLE 1

(1) Detection of Hybrid DNA Fragment using Fluorescent Intercalator

The fluorescent intercalator (1 M) prepared above was placed in an aqueous 5 mM phosphate buffer solution (pH 7.0) containing a calf thymus DNA (hybrid DNA, 100 μM) and sodium sulfate (5 mM). In the buffer solution, the fluorescent intercalator was intercalated into the hybrid DNA. The fluorescence emitted by the buffer solution containing the hybrid DNA having the intercalated fluorescent intercalator was fluorometrically measured in the wavelength region of 440 to 600 nm by exciting with a light of 434 nm.

The fluorescence emitted by the same buffer solution containing no calf thymus DNA (i.e., hybrid DNA) was also measured in the same manner.

It was found that the fluorescence strength at 475 nm measured from the buffer solution containing hybrid DNA was approx. 30 times as much as the florescence strength measured from the buffer solution containing no hybrid DNA.

(2) Measurement of Rate of Dissociation of Intercalator from Hybrid DNA

To the buffer solution containing hybrid DNA and intercalator which was employed above was added an aqueous sodium dodecylsulfate (SDS) solution to give a final SDS concentration of 0.5 vol. %. After the SDS solution was added, variation of the fluorescence strength at a lapse of time was measured. From the variation data, the dissociation rate was determined. The dissociation rate was 0.02/sec.

Comparison Example 1

The same calf thymus DNA (hybrid DNA) as employed in Example 1 was heated to 90° C. for 20 min., to give a single stranded DNA.

The procedures of Example 1 were repeated using thus prepared single stranded DNA in place of the hybrid DNA.

It was found that the fluorescence strength at 475 nm measured from the buffer solution containing single stranded DNA was approx. 16 times as much as the florescence strength measured from the buffer solution containing no single stranded DNA. The dissociation rate determined in the same manner as in Example 1 was 1.2/sec.

Comparison Example 2

The procedures of Example 1 were repeated using a known fluorescent intercalator (below described 9-amino-6-chloro-2-methoxyacridine, available from Molecular Probe, Inc.) in place of the fluorescent intercalator compound of the invention.

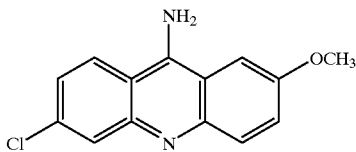

It was found that the fluorescence strength at 475 nm measured from the buffer solution containing the hybrid DNA and the known fluorescent intercalator was approx. 6 times as much as the florescence strength measured from the buffer solution containing no hybrid DA. The dissociation rate determined in the same manner as in Example 1 was 19.0/sec.

Comparison Example 3

The procedures of Exarrple 1 were repeated using a known fluorescent intercalator (aforementioned N,N-bis{3-[4-(3-(6-chloro-9-imino-2-methoxyacridinyl)propyl)-1,4- diazacyclohexyl]propyl}naphthalenediimide, having a pair of fluorescent moieties) in place of the fluorescent intercalator compound of the invention.

It was found that the fluorescence strength at 475 nm measured from the buffer solution containing the hybrid DNA and the known fluorescent intercalator was not high, as compared with the florescence strength measured from the buffer solution containing no hybrid DNA. This means that S/N ratio of the detection is not high.

What is claimed is:

1. A water-soluble fluorescent intercalator compound having the formula:

in which F is a fluorescent moiety, X is a cyclic group selected from the group consisting of a naphthalene diimide group, an anthraquinone group, or an anthracene group, and La is a linking group, containing one or more groups selected from the group consisting of an amino bonding, an ester bonding, an ether bonding, a thioether bonding, a diimide bonding, a thiodiimide bonding, a thioamide bonding, an imino bonding, a carbonyl bonding, a thiocarbonyl bonding, or 1,4-piperazinyl bonding, any bonding possibly having one or more substituents selected from the group consisting of hydroxyl, halogen, carboxyl, amino, cyano, nitro, formyl, formylamino, alkyl having 1 to 6 carbon atoms, alkylene having 1 to 6 carbon atoms, alkenylene having 2 to 6 carbon atoms, alkylamino having 1 to 6 carbon atoms, halogenated alkyl having 1 to 6 carbon atoms, cycloalkylamono having 5 to 7 carbon atoms, dialkylamino having 2 to 12 carbon atoms, aryl having 6 to 12 carbon atoms, aralkyl having 7 to 18 carbon atoms which contains alkyl of 1–6 carbon atoms, aralkylamino having 7 to 18 carbon atoms which contains alkyl of 1–6 carbon atoms, alkanoyl having 2 to 7 carbon atoms, alkanoylamino having 2 to 7 carbon atoms, N-alkanoyl-N-alkylamino having 3 to 10 carbon atoms, aminocarbonyl, alkoxycarbonyl having 2 to 7 carbon atoms, heterocyclic ring having 2 to 10 carbon atoms which has 1 to 4 hetero atoms such as S, N, or O, and aryl having 6 to 12 carbon atoms in its ring structure which may have 1 to 5 substituents such as alkyl of 1–6 carbon atoms, alkoxy of 1–6 carbon atoms, or halogen.

2. The compound of claim 1, wherein F is a fluorescent aromatic moiety.

3. The compound of claim 2, wherein F is a fluorescent aromatic moiety having an acridine group, an indocyanine group, or an azaindoleninecyanine group.

4. The compound of claim 1, wherein La has no aromatic group.

5. The compound of claim 1, wherein La contains at least one group selected from the group consisting of an imino group, a 1,4-piperazinyl group, —O—, —S—, —CONH—, and —SO$_2$—.

6. The compound of claim 1, wherein a main chain of La contains 2 to 50 atoms, which are counted along the shortest connection route from F to X.

7. A water-soluble fluorescent intercalator compound having the formula:

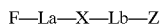

in which F is a fluorescent moiety, X is a cyclic group selected from the group consisting of a naphthalene diimide group, an anthraquinone group or an anthracene group, La is a linking group, containing one or more groups selected from the group consisting of an amino bonding, an ester bonding, an ether bonding, a thioether bonding, a diimide bonding, a thiodiimide bonding, a thioamide bonding, an imino bonding, a carbonyl bonding, a thiocarbonyl bonding, or 1,4-piperazinyl bonding, any bonding possibly having one or more substituents selected from the group consisting of hydroxyl, halogen, carboxyl, amino, cyano, nitro, formyl, formylamino, alkyl having 1 to 6 carbon atoms, alkylene which contains 1 to 6 carbon atoms, alkenylene having 2 to 6 carbon atoms, alkylamino having 1 to 6 carbon atoms, halogenated alkyl having 1 to 6 carbon atoms, cycloalkylamono having 5 to 7 carbon atoms, dialkylamino having 2 to 12 carbon atoms, aryl having 6 to 12 carbon atoms, aralkyl having 7 to 18 carbon atoms which contains alkyl of 1–6 carbon atoms, aralkylamino having 7 to 18 carbon atoms which contains alkyl of 1–6 carbon atoms, alkanoyl having 2 to 7 carbon atoms, alkanoylamino having 2 to 7 carbon atoms, N-alkanoyl- N-alkylamino having 3 to 10 carbon atoms, aminocarbonyl, alkoxycarbonyl having 2 to 7 carbon atoms, heterocyclic ring having 2 to 10 carbon atoms which has 1 to 4 hetero atoms which may be S, N, or O, and aryl having 6 to 12 carbon atoms in its ring structure which may have 1 to 5 substituents such as alkyl of 1–6 carbon atoms, alkoxy of 1–6 carbon atoms, or halogen.

8. The compound of claim 7, wherein Z is a non-fluorescent, non-aromatic moiety.

9. The compound of claim 8, wherein Z is a non-fluorescent, non-aromatic moiety containing at least one atom selected from the group consisting of oxygen, nitrogen and sulfur.

10. The compound of claim 9, wherein Z is a non-fluorescent, non-aromatic moiety having at least one group selected from the group consisting of an amino group, a carboxyl group, a sulonic acid group, a sulfinic acid group, a sulfenic acid group, a hydrazino group, a carbamoyl group, a hydroxyl group, an imino group, and a mercapto group.

11. The compound of claim 7, wherein a main chain of La—X—Lb contains 10 to 100 atoms, which are counted along the shortest connection route from F to Z.

12. A process for fluorometrically detecting oligonucleotide samples or polynucleotide samples complementary to a group of probe molecules of nucleotide derivatives or their analogues fixed onto a substrate, which comprises the steps of:

bringing the group of probe molecules into contact with oligonucleotide samples or polynucleotide samples in an aqueous medium in the presence of a fluorescent intercalator compound having one of the following formulas:

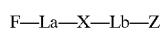

in which F is a fluorescent moiety, X is a cyclic group, La is a linking group, containing one or more groups selected from the group consisting of an amino bonding, an ester bonding, an ether bonding, a thioether bonding, a diimide bonding, a thiodiimide bonding, a thioamide bonding, an imino bonding, a carbonyl bonding, a thiocarbonyl bonding, or 1,4-piperazinyl bonding, any bonding possibly having one or more substituents selected from the group consisting of hydroxyl, halogen, carboxyl, amino, cyano, nitro, formyl, formylamino, alkyl having 1 to 6 carbon atoms, alkylene having 1 to 6 carbon atoms, alkenylene having 2 to 6 carbon atoms, alkylamino having 1 to 6 carbon atoms, halogenated alkyl having 1 to 6 carbon atoms, cycloalkylamono having 5 to 7 carbon atoms, dialkylamino having 2 to 12 carbon atoms, aryl having 6 to 12 carbon atoms, aralkyl having 7 to 18 carbon atoms which contains alkyl of 1–6 carbon atoms, aralkylamino having 7 to 18 carbon atoms which contains alkyl of 1–6 carbon atoms, alkanoyl having 2 to 7 carbon atoms, alkanoylamino having 2 to 7 carbon atoms, N-alkanoyl-N-alkylamino having 3 to 10 carbon atoms, aminocarbonyl, alkoxycarbonyl having 2 to 7 carbon atoms, heterocyclic ring having 2 to 10 carbon atoms which has 1 to 4 hetero atoms such as S, N, or O, and aryl having 6 to 12 carbon atoms in its ring structure which may have 1 to 5 substituents such as alkyl of 1–6 carbon atoms, alkoxy of 1–6 carbon atoms, or halogen, so as to form by hybridization a complex of the group of probe molecules and the oligonucleotide samples or polynucleotide samples on the substrate in which the fluorescent intercalator compound is intercalated; and detecting a fluorescence emitted from the fluorescent intercalator compound intercalated into the hybridized complex on the substrate.

13. A process for fluorometrically detecting oligonucleotide samples or polynucleotide samples complementary to a group of probe molecules of nucleotide derivatives or their analogues fixed onto a substrate, which comprises the steps of:

bringing the group of probe molecules into contact with oligonucleotide samples or polynucleotide samples in an aqueous medium so as to form by hybridization a complex of the group of probe molecules and the oligonucleotide samples or polynucleotide samples on the substrate;

bringing a fluorescent intercalator compound having one of the following formulas:

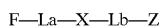

in which F is a fluorescent moiety, X is a cyclic group, La is a linking group, containing one or more groups selected from the group consisting of an amino bonding, an ester bonding, an ether bonding, a thioether bonding, a diimide bonding, a thiodiimide bonding, a thioamide bonding, an imino bonding, a carbonyl bonding, a thiocarbonyl bonding, or 1,4-piperazinyl bonding, any bonding possibly having one or more substituents selected from the group consisting of hydroxyl, halogen, carboxyl, amino, cyano, nitro, formyl, formylamino, alkyl having 1 to 6 carbon atoms, alkylene which contains 1 to 6 carbon atoms, alkenylene having 2 to 6 carbon atoms, alkylamino having 1 to 6 carbon atoms, halogenated alkyl having 1 to 6 carbon atoms, cycloalkylamono having 5 to 7 carbon atoms, dialkylamino having 2 to 12 carbon atoms, aryl having 6 to 12 carbon atoms, aralkyl having 7 to 18 carbon atoms which contains alkyl of 1–6 carbon atoms, aralkylamino having 7 to 18 carbon atoms which contains alkyl of 1–6 carbon atoms, alkanoyl having 2 to 7 carbon atoms, alkanoylamino having 2 to 7 carbon atoms, N-alkanoyl-N-alkylamino having 3 to 10 carbon atoms, aminocarbonyl, alkoxycarbonyl having 2 to 7 carbon atoms, heterocyclic ring having 2 to 10 carbon atoms which has 1 to 4 hetero atoms such as S, N, or O, and aryl having 6 to 12 carbon atoms in its ring structure which may have 1 to 5 substituents such as alkyl of 1–6 carbon atoms, alkoxy of 1–6 carbon atoms, or halogen into contact with the hybridized complex on the substrate, whereby the fluorescent intercalator compound is intercalated into the hybridized complex; and detecting a fluorescence emitted from the fluorescent intercalator compound intercalated into the hybridized complex on the substrate.

14. The compound of claim 1 wherein La contains an alkylene group having 1 to 6 carbon atoms and alkenylene group having 2 to 6 carbon atoms and the number of substituents is in the range from 1 to 12.

15. The compound of claim 1 wherein La contains an alkenylene group having 2 to 6 carbon atoms and the number of substituents is from 1 to 10.

16. The compound of claim 12 wherein Lb contains an alkylene having 1 to 6 carbon atoms group and alkenylene group having 2 to 6 carbon atoms and the number of substituents is from 1 to 12.

17. The compound of claim 12 wherein Lb contains an alkenylene group having 2 to 6 carbon atoms and the number of substituents is from 1 to 10.

18. The compound of claim 13 wherein Z contains an alkylene group having 1 to 6 carbon atoms and alkenylene group having 2 to 6 carbon atoms and the number of substituents is from 1 to 12 .

19. The compound of claim 13, wherein Z contains an alkenylene group having 2 to 6 carbon atoms and the number of substituents is from 1 to 10 .

20. The compound of claim 7 wherein Lb contains an alkylene group having 1 to 6 carbon atoms and alkenylene group having 2 to 6 carbon atoms and the number of substituents is from 1 to 12.

21. The compound of claim 7, wherein Lb contains an alkenylene group having 2 to 6 carbon atoms and the number of substituents is from 1 to 10 .

22. A water- soluble fluorescent intercalator compound having the formula:

in which F is a fluorescent moiety, La is a linking group, and x is a naphthalene diimide group, an anthraquinone group, or an anthracene group.

* * * * *